United States Patent
Kavanagh et al.

(10) Patent No.: US 6,578,709 B1
(45) Date of Patent: Jun. 17, 2003

(54) URINARY CATHETER PACKAGE AND LUBRICATOR THEREFOR WITH COMBINED GRIPPING AND SEALING MEANS

(75) Inventors: Seamus T. Kavanagh, Ballina (IE); Martin P. Creaven, Ballina (IE); Thorsten Rodtmann, Drumshanbo (IE); Sean Sweeney, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 197 days.

(21) Appl. No.: 09/910,500

(22) Filed: Jul. 19, 2001

(51) Int. Cl.$^7$ .................................................. A61F 5/44
(52) U.S. Cl. ...................... 206/364; 206/571; 604/328; 604/346
(58) Field of Search ................. 206/571, 363, 206/364; 604/328, 327, 329, 330, 331, 346, 349, 265

(56) References Cited

U.S. PATENT DOCUMENTS

| | | | |
|---|---|---|---|
| 3,556,294 A | 1/1971 | Walck, III | |
| 3,854,483 A | 12/1974 | Powers | |
| 3,934,721 A | 1/1976 | Juster et al. | |
| 4,062,363 A | 12/1977 | Bonner, Jr. | |
| 4,230,115 A | 10/1980 | Walz, Jr. et al. | |
| 4,235,232 A | 11/1980 | Spaven et al. | |
| 4,652,259 A | 3/1987 | O'Neil | |
| 5,147,341 A | 9/1992 | Starke et al. | |
| 5,226,530 A | 7/1993 | Golden | |
| 5,230,428 A | * 7/1993 | McShane | 206/363 |
| 5,454,798 A | 10/1995 | Kubalak et al. | |
| 5,895,374 A | * 4/1999 | R.o slashed.dsten | 604/163 |
| 6,004,305 A | 12/1999 | Hursman et al. | |
| 6,053,905 A | 4/2000 | Daignault, Jr. et al. | |

FOREIGN PATENT DOCUMENTS

| | | |
|---|---|---|
| DE | 0 677 299 B1 | 4/2001 |
| WO | WO 98/06642 | 2/1998 |

* cited by examiner

*Primary Examiner*—Jacob K. Ackun
(74) *Attorney, Agent, or Firm*—Marshall, Gerstein & Borun

(57) ABSTRACT

A urinary catheter package takes the form of a pouch containing a catheter and a lubricating device. The lubricating device comprises a housing with distal and proximal end portions and a lubricant-containing chamber therebetween. A frusto-conical collar at the proximal end of the device performs dual functions of preventing lubricant leakage into the pouch and unintentional sliding movement of the catheter when the package is in use.

57 Claims, 2 Drawing Sheets

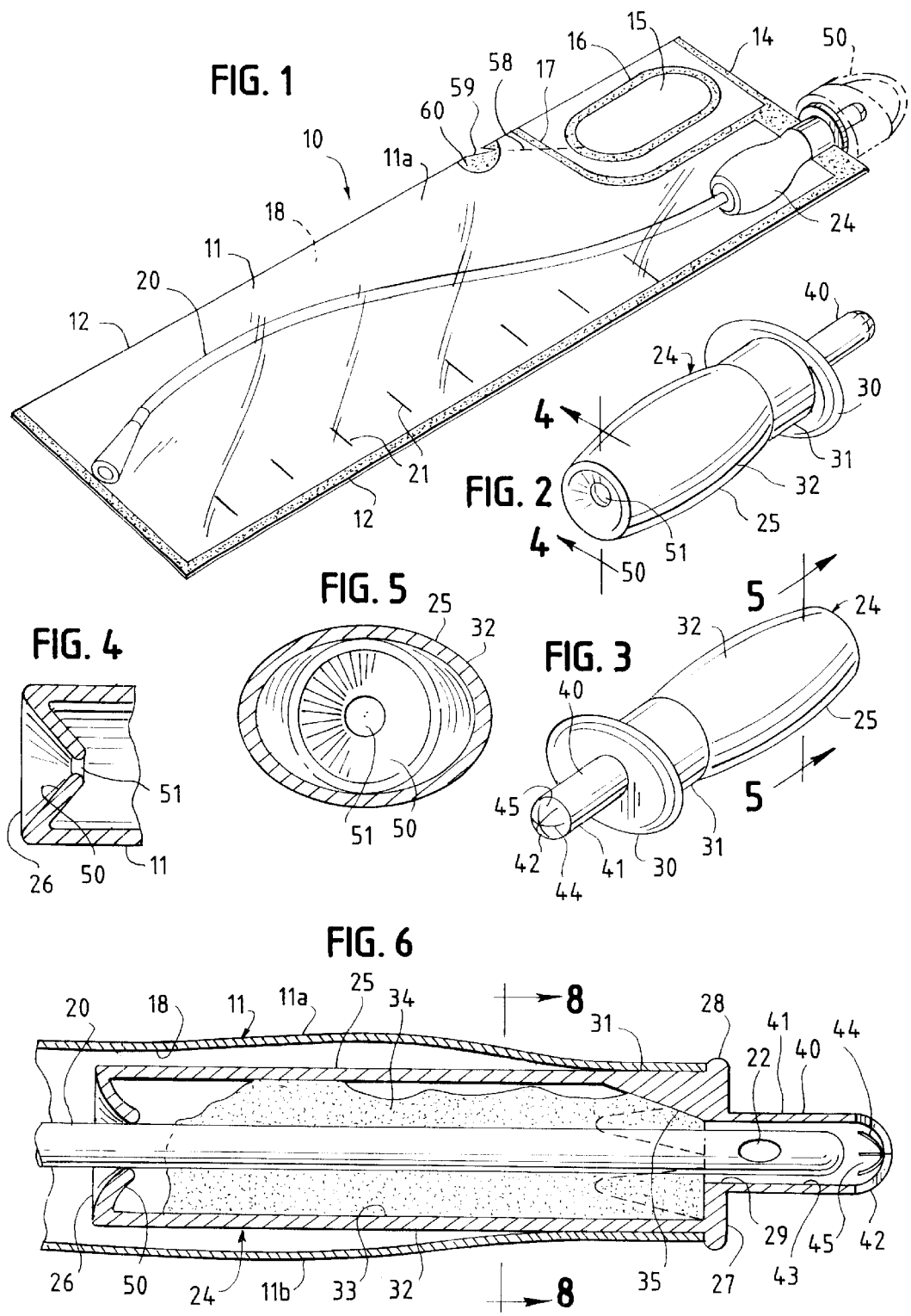

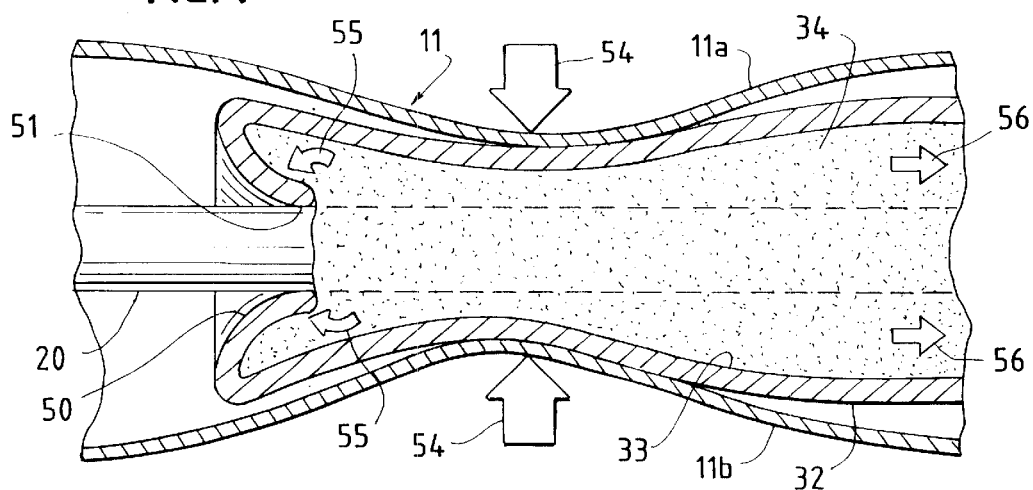
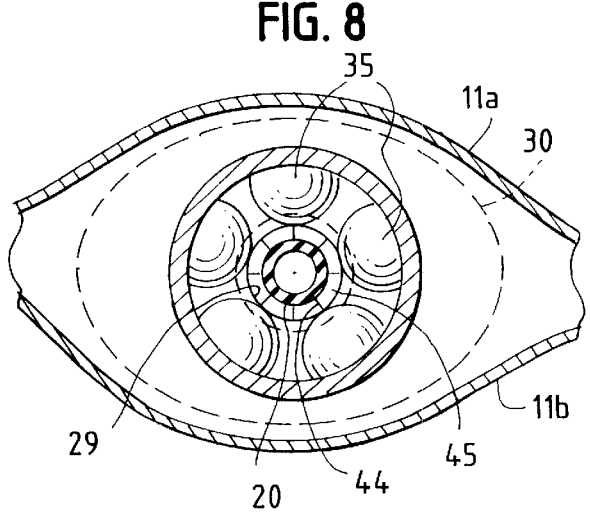
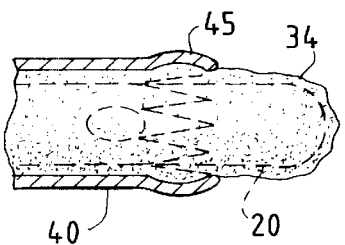
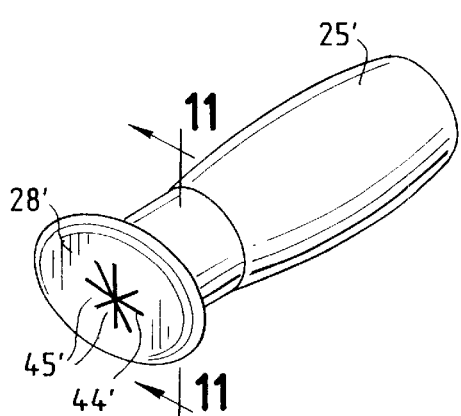
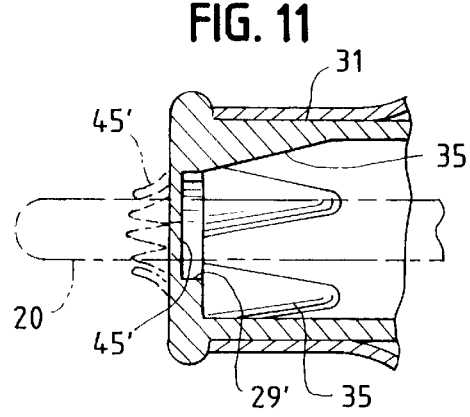

URINARY CATHETER PACKAGE AND LUBRICATOR THEREFOR WITH COMBINED GRIPPING AND SEALING MEANS

BACKGROUND AND SUMMARY OF THE INVENTION

Urinary catheters for draining the bladder through the urethra are commonly packaged in sterile and pre-lubricated condition in flexible containers or pouches. In some cases, the catheters are intended to be fully removed from such containers at the time of catheterization, whereas in others the containers and catheters may remain in communication with the containers then serving as urine-collecting pouches. Reference may be had to U.S. Pat. No. 3,854,483 (Powers), U.S. Pat. No. 5,226,530 (Golden), U.S. Pat. No. 3,934,721 (Juster et al), U.S. Pat. No. 6,004,305 (Hursman et al), U.S. Pat. No. 5,147,341 (Starke et al) and U.S. Pat. No. 6,053,905 (Daignault et al) as illustrative of the art.

Catheterization commonly involves inserting the distal tip of a catheter (sometimes protected against contamination by an introducer sleeve as disclosed, for example, in U.S. Pat. Nos. 3,854,483 and 4,652,259) into the urethra and then longitudinally collapsing and extending the pouch in an accordion-like manner until the tip reaches the bladder. Such action is illustrated, for example, in U.S. Pat. No. 4,062,363 (Bonner). By gripping the remote (proximal) end of the catheter between the walls of the pouch during the pouch-collapsing phase, the catheter is advanced in a distal direction and, conversely, during the pouch-extending phase, the catheter is held against reverse sliding movement by gripping it between the pouch walls near the pouch's distal end. The operation is a two-handed one requiring considerable dexterity to insure that the catheter is advanced during the pouch-collapsing phase and not retracted during the pouch-extending phase.

Complications may arise that make such a procedure even more difficult. For example, fluid pressure may tend to expel the catheter and require the user to continue gripping the catheter between the walls of the pouch to hold it in place during voiding. Because the catheter is lubricated, immobilizing it by applying a gripping force to the walls of the pouch may require more strength and dexterity than patients can provide, thereby precluding self-catheterization.

In an effort to reduce such problems, some packages for prelubricated catheters contain gripping devices that may be squeezed to help hold a catheter against reverse sliding movement (see U.S. Pat. Nos. 6,053,905, 6,004,305 and WO 98/06642). Typically, such gripping devices are designed to engage the side surfaces of a catheter but, since those surfaces are already lubricated, slippage may still readily occur.

Lubricating and gripping systems used in current catheter packages often have other shortcomings as well. Lubricant gel or liquid may not be retained in one area of such a package but may be free to migrate into the urine-collective chamber, causing the walls of the pouch to stick together and make voiding more difficult. Squeezable gripping devices, even if properly fitted onto the tip of a catheter during production, may slip off during storage and transport, requiring a user to refit such a device prior to catheterization. Further, in some constructions, lubricant tends to be unevenly distributed over the surfaces of a catheter, causing patient discomfort and risking possible injury during catheterization.

This invention therefore concerns an improved self-lubricating catheter package, and particularly an improved lubricator therefor, that overcome or at least greatly reduce the aforementioned defects and disadvantages of current products. More specifically, this invention involves a catheter package in which a flowable lubricant (preferably in the form of a gel) is retained in a guide housing located within the distal end of the pouch. Means are provided to ensure even distribution of the lubricant over the surfaces of a catheter during a catheterization procedure. The guide housing is formed of deformable and shape-recoverable material and has at its proximal end a frusto-conical wall or collar that grips unlubricated surface portions of a catheter and prevents unintentional sliding movement of the catheter during a catheterization procedure. More specifically, the tensioned collar restrains the catheter against longitudinal sliding movement until such time as an axial force is applied to the catheter that exceeds a selected threshold value. In addition to restraining unintended movement of the catheter relative to the lubricant housing, the collar effectively prevents the leakage of lubricant from the housing into the pouch.

The pouch is preferably flat and may serve as a urine-receiving container as well as a protective covering for maintaining the catheter in sterile condition prior to use. Preferably, but not necessarily, the walls of the pouch are sufficiently transparent so that the guide housing is visible through the walls of the pouch. The housing has a distal end portion of generally cylindrical configuration and a bulbous body portion, which at least in one embodiment is of oval cross section, extending between the housing's proximal and distal end portions. Where an oval shape is provided, the housing is preferably secured within the pouch so that the major axis of the oval extends along a plane parallel with and interposed between the coplanar side walls of the pouch.

The housing's distal end portion includes an end wall having an opening for advancement of a catheter therethrough during the catheterization procedure. In one embodiment of the invention, an integral introducer sleeve projects distally from the distal end wall and terminates in a rounded end having a multiplicity of crossed diametrically-extending slits defining a circumferential series of at least six, and preferably eight, radially-extending and inwardly-tapering flaps. In another embodiment, the introducer sleeve is omitted and a similar array of inwardly-extending flaps is formed instead in the distal end wall of the lubricant housing.

In each embodiment, the cylindrical distal end portion of the lubricant housing may have an internal series of circumferentially-spaced stiffening ribs. Such ribs are generally semi-conical in configuration and not only stiffen or rigidify the distal end portion of the lubricant housing but also help to direct the tip of a catheter towards the opening in the housing's distal end and into the passageway of the introducer sleeve if the embodiment is equipped with such a sleeve. Of particular importance is the fact that the opening defined by the ribs, as well as the opening through the distal end wall and the passageway of the introducer sleeve, are all substantially greater in diameter than the outside diameter of the catheter to be advanced therethrough. As the catheter is so advanced, and as the body portion of the lubricant chamber is gripped between the walls of the pouch and is preferably squeezed not only to hold the assembly but also to cause the distal displacement of lubricant, the outer surfaces of the catheter receives an even coating of flowable lubricant material. Because of the relatively large size of the distal opening (and of the introducer passageway) and the multiplicity of flexible flaps, the lubricant that is applicable to the catheter remains evenly distributed on its surfaces as the catheter enters urethra.

Other advantages, features and objects of the invention will become apparent from the specification and drawings.

DRAWINGS

FIG. 1 is a perspective view of a catheter package embodying this invention.

FIG. 2 is a perspective view of the lubricant housing taken from the proximal end thereof.

FIG. 3 is a perspective view of the lubricant housing taken from its distal end.

FIG. 4 is a fragmentary longitudinal sectional view taken along line 4—4 of FIG. 2.

FIG. 5 is a cross sectional view taken along line 5—5 of. FIG. 3.

FIG. 6 is a longitudinal sectional view showing the distal end portion of the package.

FIG. 7 is an enlarged fragmentary longitudinal sectional view illustrating action of the ceiling and catheter-restraining collar when the package is squeezed.

FIG. 8 is a cross sectional view taken along line 8—8 of FIG. 6.

FIG. 9 is a fragmentary sectional view illustrating operation of the introducer sleeve during a catheterization procedure.

FIG. 10 is a perspective view of a guide housing constituting a second embodiment of the invention.

FIG. 11 is a fragmentary longitudinal sectional view taken along line 11—11 of FIG. 10.

DETAILED DESCRIPTION OF PREFERRED EMBODIMENTS

In the drawings, the numeral 10 generally designates a sterile self-lubricating catheter package comprising a container in the form of a flat, elongated pouch or bag 11 having top and bottom walls 11a and 11b preferably formed of heat-sealable thermoplastic film. In the particular embodiment illustrated, the pouch is generally rectangular in outline with longitudinal edges 12, proximal end 13, and distal end 14. The pouch may be formed as a rectangular sheet folded upon itself and heat sealed along longitudinal edge portion and edge portions at its distal and proximal ends as shown in FIG. 1. Alternatively, the pouch may be formed as an extruded tube with its proximal and distal ends closed by heat seals. The terms "top" and "bottom" are used here in referring to walls 11a and 11b to facilitate description of the assembly as a whole but, in view of the symmetry of the pouch, it will be understood that these terms are arbitrary and that the pouch may just as easily be placed on a support of surface in flipped over condition with 11b constituting the top wall and 11a the bottom wall. Also, while a rectangular configuration is shown, that shape is not considered critical.

In the embodiment depicted in FIG. 1, an oval-shaped opening 15, edged by heat seal 16, may be formed through both walls of the pouch to facilitate handling of the pouch and allow it to be suspended from a suitable support. Heat seal 17 separates the apertured corner portion of the pouch from the compartment 18 that contains urinary catheter 20. A main purpose of the compartment 18 is to maintain the catheter in sterile condition but, if desired, the compartment may also be of sufficient size to receive and collect urine expelled during catheterization. For that purpose, one or both of the side walls of the pouch may be provided with volume indica 21 (FIG. 1). Alternatively, the pouch may be of different shape than shown and may serve simply as an enclosure to maintain the contents in sterile condition prior to use.

Catheter 20 is a standard urinary catheter of tubular shape formed of soft, flexible, thermoplastic material. One or more openings 22 are provided at its distal end. At its proximal end, the catheter may have a fitting 23 which prevents or restrains extraction of the catheter from the pouch and, if desired, may also be used as a Luer fitting for attachment to a syringe or other suitable device. Alternatively, fitting 23 may be omitted and some other fitting, which may or may not operate as a stop member, may be provided.

The catheter gripping and lubricating device 24 takes the form of a generally tubular guide housing 25 having proximal and distal end portions 26 and 27, respectively. Ideally, the housing is integrally formed of an elastomeric material such as silicone rubber and is therefore deformable, stretchable, and shape-recoverable. The housing's distal end portion includes an end wall 28 having a central opening 29, an oval-shaped flange 30 that constitutes an outward extension of the end wall, and a generally cylindrical wall portion 31 (FIGS. 2, 3). An enlarged body portion 32 of the housing bulges laterally outwardly and, as shown most clearly in FIG. 5, may be generally oval in cross section. The orientation is such that the major axis of the oval lies along a plane that is generally parallel with the side walls 11a and 11b of the pouch.

While in the preferred embodiment shown the guide housing 25 is formed integrally and entirely of soft, deformable and shape-recoverable material, ideally an elastomeric material, variations are possible that may still achieve some of the advantages of the illustrated embodiment. Thus, the housing might be formed of two or more sections or pieces permanently joined together with such sections being of identical or different materials. It is essential that the proximal and distal end portions 26 and 27, or at least certain wall portions thereof, be deformable and shape-recoverable, but such properties are of lesser importance for the body portion 32. If the body portion were formed of a different material, even one that were relatively stiff or rigid, some of the benefits of this invention might still be achieved although to a lesser extent.

The housing 25 defines a chamber 33 that contains a body of lubricant 34 (FIG. 6). The lubricant is a flowable liquid or gel and may be any of a variety of materials commonly used for lubricating urinary catheters. Its viscosity may be varied from that of a readily flowable oil to that of a more viscose semi-liquid. A lubricant gel is generally preferred. Such a lubricant is preferably, but not necessarily, water soluble.

Opening 29 at the distal end portion of the housing is substantially larger in diameter than the outside diameter of the catheter 20 to be advanced therethrough. A plurality of stiffening ribs 35 are located within the distal end portion 27 of the housing and function to direct catheter 20 towards opening 29 as well as to stiffen or rigidify the cylindrical neck portion adjacent end wall 28. Each rib is generally semi-conical in shape with its apex facing proximally and its base merging with distal end wall 28. While five such ribs are shown in FIG. 8, a greater or smaller number might be provided as desired. Of particular importance is the fact that the opening circumscribed by the ribs at their distal ends is still substantially larger than the outside diameter of catheter 20. Lubricant 34 may readily flow between the ribs and through opening 29 when the bulbous body portion 32 is squeezed or compressed as described more fully hereinafter.

The embodiment of the catheter gripping and lubricating device illustrated in FIGS. 1–9 includes a soft deformable and shape-recoverable introducer sleeve 40 having a tubular portion 41 and a rounded end portion 42. The introducer sleeve is formed as an integral part of the distal end portion 27 the housing and projects distally from end wall 28. The lumen 43 of the introducer sleeve is sized to match opening 29 and communicates with chamber 33 of the housing through that opening. The length of the introducer is such that, upon insertion into the urethra, it shields the catheter 20 against contact with and contamination by a short stretch of the urethra adjacent the labia.

As shown in FIGS. 3, 6 and 9, the rounded end 42 of the introducer sleeve 40 has a plurality of crossed diametrically-extending slits 44 that together define a multiplicity of end flaps 45. Each of the identical end flaps is of limited angular dimension. Specifically, there should be at least six, and preferably eight such flaps with each flap having a width at its base of no more than 60° and preferably only 45°. It has been found that such limited base width does not significantly restrain flexing action of the flaps into the open positions depicted in FIG. 9 and insures that a substantially even coating of lubricant remains on the catheter as it advances beyond the introducer sleeve.

The introducer sleeve 40 and flange 30 may be maintained in sterile condition prior to a catheterization procedure by any suitable protective means. In FIG. 1, such means takes the form of a removable end cap 50 (shown in phantom). Alternatively, the entire package 10 may be enclosed in sterile condition in an outer protective envelope or wrapper (not shown).

The catheter gripping and sealing means at the proximal end portion of the housing comprises an end wall or collar 50 that is preferable but not necessarily formed integrally with the remainder of the housing. In any case, end wall 50 should be deformable, stretchable, and shape recoverable, preferably being formed of an elastomeric material as already indicated. FIG. 4 reveals that the end wall 50 in an untensioned and undeformed state is frusto-conical in shape. It tapers distally and has an opening 51 at its truncated distal end. Opening 51 is circular in shape and has a diameter substantially smaller than the outside diameter of catheter 20. As a catheter is forced into the housing, the conical wall or collar 50 flexes and stretches outwardly and distally as shown in FIG. 6 with the edges defining opening 51 firmly and sealingly engaging unlubricated outer surface portions of the catheter. End wall 50 therefore performs the dual functions, first, of preventing the escape of lubricant in a proximal direction from the housing, and second, of gripping the catheter to restrain its longitudinal movement until a threshold level of axial force is applied.

FIG. 7 somewhat schematically depicts how the conical wall or collar 50 acts to prevent leakage of lubricant 34 in a proximal direction even when the bulbous lubricant-containing portion 32 of the housing is squeezed as indicated by arrows 54. Such deformation of the housing tends to cause displacement of lubricant, but proximal displacement represented by arrows 55 urges the edges of conical wall 50 even more tightly into sealing contact with a catheter 20. Hence, displacement of lubricant tends to occur more in a distal direction as indicated by arrows 56. Whether such displacement results in lubricant being forced into introducer 40 depends in part on the volume of lubricant within chamber 33 and the extent to which the chamber is squeezed, but distal flow of lubricant into the introducer is considered advantageous.

At the time of catheterization, a user holds housing 25 in place by gripping the bulbous portion 32 between walls 11a and 11b of the pouch. Such gripping force normally causes some deformation of portion 32 housing, although not necessarily as substantially as shown in FIG. 7. With the fingers of the other hand, the user grips the proximal end portion of the catheter between walls 11a and 11b of the pouch and urges the catheter distally. Such action causes the pouch walls to collapse longitudinally, producing accordion-like folds as the pouch's proximal end approaches guide housing 25. The user then draws the proximal end of the pouch outwardly into its original unfolded condition, with the gripping force applied by the conical wall or collar 50 of the housing preventing retrograde sliding movement of the catheter, and repeals the process until the tip of the catheter has passed through the urethra and reaches the bladder. If the pouch is to be used as a fluid collection device, urine flowing through catheter passes into the chamber of the pouch. The pouch later may be emptied by tearing it along indicia line 58 extending from notch 59 to oval opening 15 (FIG. 1). A starting notch is preformed in a heat-sealed area 60 so that no leakage occurs until the package is torn open along line 58 to form what effectively functions as a corner pouring spout.

The embodiment of FIGS. 10 and 11 is identical to what has already been described except that housing 25' has no introducer projecting from its distal end wall 28'. Instead, end wall 28' has an opening 29' that is normally closed by a multiplicity of at least six, and preferably eight, flaps 45' formed by diametrically-extending slits 44'. Opening 29' is substantially larger than the outside diameter of catheter 20 and, because the multiplicity of narrow flaps 45' may easily flex distally to allow the advancement of catheter 20, lubricant applied to the surfaces of the catheter in the chamber of the housing remains on those surfaces as the catheter enters a patient's urethra.

While in the foregoing we have disclosed embodiments of the invention in considerable detail for purposes of illustration, it will be understood by those skilled in the art that many of these details may be varied without departing from the spirit and scope of the invention.

What is claimed is:

1. A lubricating device for a urinary catheter, comprising a guide housing having proximal and distal end portions defining a lubricant chamber therebetween; a body of lubricant within said chamber; said proximal end portion including a first end wall having an opening therethrough for receiving a catheter extending through said opening and into said body of lubricant; said first end wall being deformable and shape-recoverable and having edges defining said opening for firmly and sealingly engaging unlubricated outer surface portions of a catheter for restraining longitudinal movement of such catheter until a threshold level of axial force is applied thereto.

2. The device of claim 1 in which a urinary catheter extends through said opening and into said lubricant chamber.

3. The device of claim 2 in which said opening, when said first end wall is undeformed, has a diameter smaller than the outside diameter of a catheter to be extended therethrough.

4. The device of claim 3 in which said first end wall is fruto-conical in shape with a taper extending in a distal direction.

5. The device of claim 1, 2, 3 or 4 in which said lubricant is a lubricant gel.

6. The device of claim 1 in which said distal end portion of said housing is generally cylindrical; said housing having a bulbous body portion between said proximal and distal end portions.

7. The device of claim 6 in which said body portion is of oval cross section.

8. The device of claim 1 in which said distal end portion includes a second end wall having a opening for advancement of a catheter therethrough.

9. The device of claim 8 in which said housing includes a passage-defining introducer sleeve projecting distally from said second end wall and communicating directly with said opening thereof.

10. The device of claim 9 in which said passage of said introducer sleeve and said opening of said seconds end wall have diameters substantially larger than the outside diameter of a catheter extendable therethrough.

11. The device of claim 9 or 10 in which said introducer sleeve is formed of soft, deformable and shape-recoverable material and has a rounded distal end wall with a multiplicity of crossed diametrically-extending slits defining a series of at least six radially inwardly tapering flaps.

12. The device of claim 11 in which there are eight of said flaps.

13. The device of claim 8 in which said second end wall is formed of deformable and shape-recoverable material and has a multiplicity of crossed slits defining a circumferential series of inwardly-tapering flaps for closing said opening of said second end wall until a catheter is advanced therethrough.

14. The device of claim 13 in which there are-at least six of said flaps with each of said flaps being equal in size.

15. The device of claim 14 in which there are eight of said flaps.

16. The device of claim 8 in which said distal end portion has therein a plurality of circumferentially-spaced stiffening and guiding ribs extending towards said second wall.

17. The device of claim 16 in which said ribs are located along an inside surface of said cylindrical portion and taper in a proximal direction.

18. The device of claim 1 in which said guide housing is integrally and entirely formed of soft, deformable and shape-recoverable plastic material.

19. The device of claim 18 in which said plastic material is elastomeric.

20. A urinary catheter package comprising a pouch having side walls of flexible thermoplastic film and proximal and distal ends; a urinary catheter within said pouch; and a catheter lubricating device secured within said pouch at the distal end thereof; said device comprising a guide housing having proximal and distal end portions defining a lubricant chamber therebetween; a body of lubricant within said chamber; said proximal end portion of said housing including a deformable and shape-recoverable proximal end wall having an opening therethrough with said catheter extending through said opening and into said body of lubricant; said proximal end wall having edges defining said opening in sealing contact with surfaces of said catheter for retaining lubricant against proximal displacement from said chamber; said distal end portion including a deformable and shape-recoverable distal end wall having an opening for advancement of said catheter therethrough; said distal end wall having a multiplicity of crossed slits defining a circumferential series of at least six inwardly-tapering flaps for closing said opening until said catheter is advanced therethrough.

21. The package of claim 20 in which there are eight of said flaps.

22. The package of claim 20 in which said distal end portion has therein a plurality of circumferentially-spaced stiffening and guiding ribs extending towards said distal end wall; said ribs defining a passageway substantially larger in diameter than the outside of said catheter.

23. The package of claim 21 in which said ribs taper in a proximal direction.

24. The package of claim 20 in which said side walls of said pouch are generally flat and coplanar when said pouch is empty.

25. The package of claim 24 in which said distal end portion of said housing is generally cylindrical; said housing having a bulbous body portion extending between said proximal end and distal end portion.

26. The package of claim 25 in which said bulbous body portion is of oval cross section.

27. The package of claim 26 in which said oval cross section has major and minor axes and said housing is oriented with said major axis extending parallel-with said coplanar side walls of said pouch.

28. The package of claim 20 in which said guide housing is entirely formed of soft, deformable and shape-recoverable plastic material.

29. The package of claim 28 in which said plastic material is elastomeric.

30. A urinary catheter package comprising a pouch having side walls of flexible thermoplastic film and proximal and distal ends; a urinary catheter within said pouch; and a catheter gripping and lubricating device secured within said pouch at the distal end thereof; said device comprising a deformable, and shaped-recoverable guide housing having proximal and distal end portions defining a lubricant chamber therebetween; a body of lubricant within said chamber; said proximal end portion of said housing including a first end wall having an opening therethrough with said catheter extending through said opening and into said body of lubricant; said end wall having edges defining said opening in firm sealing contact with unlubricated surfaces of said catheter for restraining longitudinal movement of said catheter until a threshold level of axial force is applied thereto.

31. The package 30 of claim in which said thermoplastic film of said pouch is transparent.

32. The package of claim 30 in which said opening of said end wall, when said housing is unstretched, has a diameter smaller than the outside diameter of said catheter.

33. The package of claim 32 in which said end wall is frusto-conical in shape with a taper thereof extending in a distal direction.

34. The package of claim 32 or 33 in which said lubricant is a lubricant gel.

35. The package of claim 32 in which said side walls of said pouch are generally flat and coplanar when said pouch is empty.

36. The package of claim 35 in which said distal end portion of said housing is generally cylindrical; said housing having a bulbous body portion of oval cross section extending between said proximal and distal end portions.

37. The package of claim 36 in which said oval cross section has major and minor axes and said housing is oriented with said major axis extending parallel with said coplanar side walls of said pouch.

38. The package of claim 36 in which said distal end portion includes a second end wall having an opening for advancement of said catheter therethrough.

39. The package of claim 38 in which said housing includes a passage-defining introducer sleeve projecting distally from said second end wall and communicating directly with said opening thereof.

40. The package of claim 39 in which said passage of said introducer sleeve and said opening of second end wall have diameters substantially larger than the outside of said catheter.

41. The package of claim 40 in which said introducer sleeve has a rounded distal end wall with a multiplicity of crossed diametrically-extending slits defining a series of at least six radially inwardly tapering flaps.

42. The package of claim 41 in which there are eight said flaps.

43. The package of claim 38 in which said second end wall has a multiplicity of crossed slits defining a circumferential series of equal-size inwardly-tapering flaps for closing said opening until said catheter is advanced therethrough.

44. The package of claim 43 in which there are at least six of said flaps.

45. The package of claim 44 in which there are eight of said flaps.

46. The package of claim 38 in which said distal end portion has therein a plurality of circumferentially-spaced stiffening and guiding ribs extending towards said second end wall; said ribs defining a passageway substantially larger in diameter than the outside of said catheter.

47. The package of claim 46 in which said ribs are located along an inside surface of said cylindrical portion and taper in a proximal direction.

48. The package of claim 30 in which said guide housing is formed integrally and entirely of elastomeric material.

49. A urinary catheter package comprising a pouch having side walls of flexible thermoplastic film and proximal and distal ends; a urinary catheter within said pouch; and a catheter lubricating device secured within said pouch at the distal end thereof; said device comprising a deformable, and shape-recoverable guide housing having proximal and distal end portions defining a lubricant chamber therebetween; a body of lubricant within said chamber; said proximal end portion of said housing including a proximal end wall having an opening therethrough with said catheter extending through said opening and into said body of lubricant; said proximal end wall having edges defining said opening in sealing contact with surfaces of said catheter for retaining lubricant in said chamber; said distal end portion of said housing including a distal end wall having an opening for advancement of said catheter therethrough; said housing including a passage-defining introducer sleeve projecting distally from said distal end wall and communicating directly with said opening thereof; said passage of said introducer sleeve and said opening of said distal end wall having diameters substantially larger than the outside of said catheter; and said introducer sleeve having a rounded distal end wall with a multiplicity of crossed diametrically-extending slits defining a series of at least six radially inwardly tapering flaps.

50. The package of claim 49 in which there are eight said flaps.

51. The package of claim 49 in which said distal end portion of said housing has a plurality of circumferentially-spaced stiffening guiding ribs disposed therein and extending towards said distal end wall; said ribs defining a passageway substantially larger in diameter than the outside of said catheter.

52. The package of claim 51 in which said ribs are located along an inside surface of said cylindrical portion and taper in a proximal direction.

53. The package of claim 49 in which said side walls of said pouch are generally flat and coplanar when said pouch is empty.

54. The package of claim 53 in which said distal end portion of said housing is generally cylindrical; said housing having a bulbous body portion extending between said proximal and distal end portions.

55. The package of claim 54 in which said bulbous body portion is of oval cross section.

56. The package of claim 54 in which said oval cross section has major and minor axes and said housing is oriented with said major axis extending parallel with said coplanar side walls of said pouch.

57. The package of claim 49 in which said guide housing is formed integrally and entirely of elastomeric material.

* * * * *

UNITED STATES PATENT AND TRADEMARK OFFICE
CERTIFICATE OF CORRECTION

PATENT NO.    : 6,578,709 B1                                                Page 1 of 1
DATED         : June 17, 2003
INVENTOR(S)   : Seamus T. Kavanagh and Martin P. Creaven It is certified that error appears in the above-identified patent and that said Letters Patent is hereby corrected as shown below:

<u>Column 7,</u>
Line 10, please delete "said seconds end wall" and insert -- said second end wall --,
Line 26, please delete "there are-at least", and insert -- there are at least --, <u>Column 8,</u>
Line 14, please delete "extending parallel-with", and insert -- extending parallel with --.

Signed and Sealed this

Eleventh Day of November, 2003

JAMES E. ROGAN
*Director of the United States Patent and Trademark Office*